(12) United States Patent
Single et al.

(10) Patent No.: US 9,566,439 B2
(45) Date of Patent: Feb. 14, 2017

(54) NEURO-STIMULATION

(75) Inventors: Peter Single, Lane Cove (AU); David Robinson, Eveleigh (AU); John Parker, Eveleigh (AU); Peter Ayre, Eveleigh (AU); Dean Karantonis, Eveleigh (AU)

(73) Assignee: SALUDA MEDICAL PTY LIMITED, Eveleigh, NSW (AU)

( * ) Notice: Subject to any disclaimer, the term of this patent is extended or adjusted under 35 U.S.C. 154(b) by 387 days.

(21) Appl. No.: 13/383,800

(22) PCT Filed: Jul. 19, 2010

(86) PCT No.: PCT/US2010/042456
§ 371 (c)(1),
(2), (4) Date: Mar. 1, 2012

(87) PCT Pub. No.: WO2011/011327
PCT Pub. Date: Jan. 27, 2011

(65) Prior Publication Data
US 2012/0161945 A1 Jun. 28, 2012

Related U.S. Application Data

(60) Provisional application No. 61/229,945, filed on Jul. 30, 2009.

(30) Foreign Application Priority Data

Jul. 20, 2009 (AU) .................................. 2009903401

(51) Int. Cl.
G08C 19/16 (2006.01)
G08B 1/08 (2006.01)
(Continued)

(52) U.S. Cl.
CPC ....... *A61N 1/36189* (2013.01); *A61N 1/36146* (2013.01); *A61N 1/05* (2013.01)

(58) Field of Classification Search
CPC ... A61N 1/05; A61N 1/36146; A61N 1/36189
(Continued)

(56) References Cited

U.S. PATENT DOCUMENTS 4,532,930 A 8/1985 Crosby et al.
4,533,988 A 8/1985 Daly et al.
(Continued)

FOREIGN PATENT DOCUMENTS

GB 2 160 743 12/1985
WO WO 97/90912 3/1997

OTHER PUBLICATIONS

G. Yang et al., "Intelligent Electrode Design for Long-Term ECG Monitoring at Home; Prototype design using FPAA and FPGA", 3$^{rd}$ International Conference on Pervasive Computing Technologies for Healthcare, Apr. 2009, 4 pages.
(Continued)

*Primary Examiner* — Emily C Terrell

(57) ABSTRACT

The invention is a distributed implantable neuro-stimulation system, comprising an implant controller including control logic to transmit two time-varying power signals, varying between two levels and out of phase with the other, and a command signal modulated onto at least one of the power signals. One or more electrode cells, each having control logic to extract charge from the power signals and recover commands from the command signal. A two-wire bus interconnecting the implant controller and all the electrode cells, to carry one of the time varying signals in each of the two wires, and to carry the command signal.

28 Claims, 13 Drawing Sheets

(51) Int. Cl.
*A61N 1/36* (2006.01)
*A61N 1/05* (2006.01)

(58) Field of Classification Search
USPC .............................. 340/12.1, 539.12; 607/45
See application file for complete search history.

(56) References Cited

U.S. PATENT DOCUMENTS

| | | | | |
|---|---|---|---|---|
| 5,593,430 | A | * | 1/1997 | Renger .............. A61N 1/36585 607/18 |
| 5,941,906 | A | * | 8/1999 | Barreras et al. ................ 607/66 |
| 5,957,958 | A | * | 9/1999 | Schulman et al. .............. 607/56 |
| 5,999,848 | A | * | 12/1999 | Gord et al. ....................... 607/2 |
| 6,445,955 | B1 | * | 9/2002 | Michelson et al. ............. 607/46 |
| 6,980,864 | B2 | | 12/2005 | Faltys et al. |
| 7,214,189 | B2 | * | 5/2007 | Zdeblick .............. A61B 5/0422 600/300 |
| 7,444,185 | B1 | | 10/2008 | Faltys et al. |
| 8,219,188 | B2 | * | 7/2012 | Craig ................................ 607/2 |
| 2004/0082946 | A1 | * | 4/2004 | Malis et al. ..................... 606/34 |
| 2005/0015133 | A1 | | 1/2005 | Ibrahim et al. |
| 2005/0197677 | A1 | * | 9/2005 | Stevenson ....................... 607/36 |
| 2005/0246002 | A1 | * | 11/2005 | Martinez ....................... 607/116 |
| 2006/0015153 | A1 | | 1/2006 | Gliner et al. |
| 2006/0173510 | A1 | * | 8/2006 | Besio et al. .................... 607/45 |
| 2008/0046025 | A1 | | 2/2008 | Tass |
| 2009/0149917 | A1 | | 6/2009 | Whitehurst et al. |
| 2011/0270349 | A1 | * | 11/2011 | Cowley ................ A61N 1/0551 607/45 |

OTHER PUBLICATIONS

N.D. Donaldson et al., "When are actively balanced biphasic ('Lilly') stimulating pulses necessary in a neurological prosthesis? 1 Historical background; Pt resting potential; Q studies" Medical and Biological Engineering and Computing, 24(1); pp. 44-49, 1986.
N.D. Donaldson et al., "When are actively balanced biphasic ('Lilly') stimulating pulses necessary in a neurological prosthesis? II pH changes; noxious products; electrode corrosion; discussion" Medical and Biological Engineering and Computing, 24(1); pp. 50-56, 1986.
PCT International Search Report and Written Opinion, PCT Applic. No. PCT/US2010/042456, filed Jul. 19, 2010, United States Searching Authority, 9 pages, Aug. 24, 2010.

\* cited by examiner

Fig. 1: eLAN system

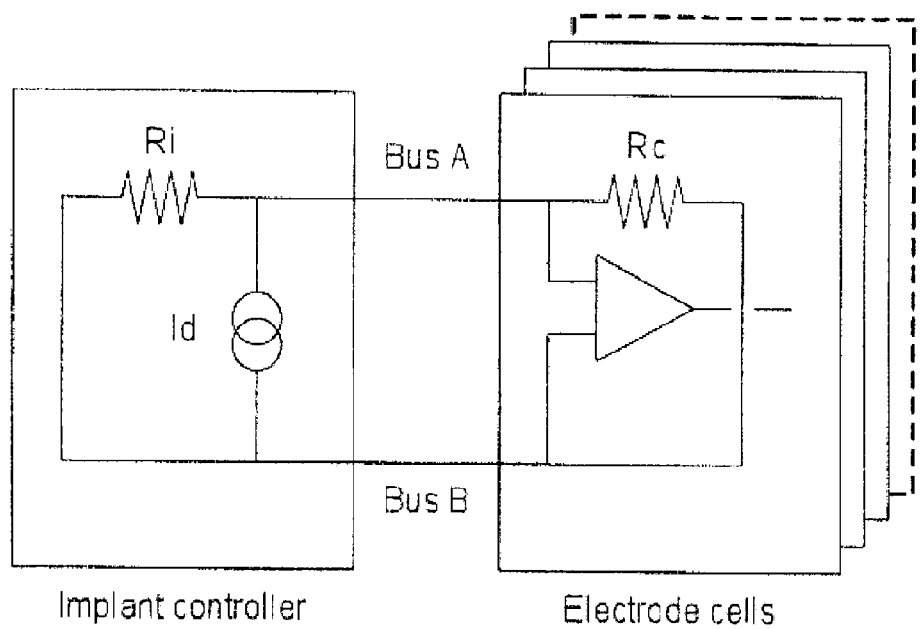
Fig. 13
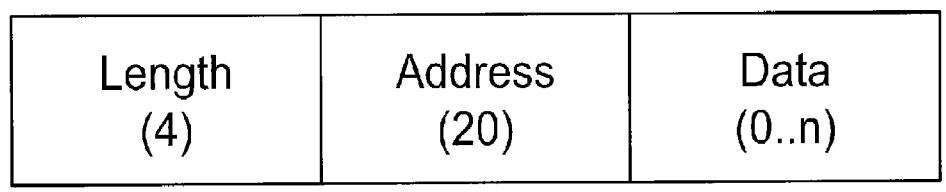
Fig. 14: Link Layer Frame

NEURO-STIMULATION

BACKGROUND OF THE INVENTION

1. Field of the Invention

This invention concerns neuro-stimulation, that is artificial electrical stimulation of body tissues using a device implanted in the body. In particular the invention concerns a distributed implantable neuro-stimulation apparatus, an electrode cell forming part of the apparatus, an implant controller forming part of the apparatus, a method of applying neuro-stimulation, and a signal for use in the method.

2. Description of Related Art

Perhaps the pacemaker is the best known tissue stimulator. It is implanted in the chest and a single electrode is connected to the heart to regulate the rate of beating. Cochlear implants are neuro-stimulators used to restore hearing. They are more complex than heart pacemakers and involve an implant controller that contains all the active electronic components, as well as twenty or so passive electrodes individually connected to the controller. The controller is sealed inside a titanium shell which has hermetic ceramic or glass feed-throughs fitted with a pin for each passive electrode. The electrodes are made from platinum and silicone, and are connected back to the controller by individual conductors. The electrodes are implanted adjacent respective parts of the cochlear to stimulate the auditory nerve.

SUMMARY OF THE INVENTION

In operation, when recovered commands select an electrode of at least one of the electrode cells to deliver a stimulus, the control logic within the selected cell may use the commands to control the selected electrode to deliver extracted charge, in cooperation with at least one other electrode.

Advantageously, a system of this type is able to control thirty-two or more electrodes, and to deliver between a hundred to thirty thousand stimuli per second, with each stimulus injecting between 100 µA and 10 mA of stimulus current. Alternatively voltage stimuli could be delivered.

The system may deliver stimuli between electrodes of a single electrode cell, electrodes of two or more electrode cells, or electrodes of one or more electrode cells and an electrode associated with the implant controller. When the stimuli are delivered using two electrodes of the same cell, then the commands received by the cell must synchronize the cooperation of the two electrodes. When more than one electrode cell is involved, the commands must synchronize the cooperation of more than one cell.

Since the control logic in the electrode cells operates to connect charge recovered from the power signal to the stimulating electrodes, there is no need to store charge in the cell, and the cell is powered down when there is no power signal; for instance in the event of a power signal failure.

Advantageously, the two-wire bus provides flexibility to the system since additional cells can be easily added; likewise cells can be removed. Different types of cells can also be mixed along the length of the bus; for instance sensor cells may be interposed with stimulating cells. The bus also facilitates replacement of the implant controller. Another advantage of the two-wire bus is that the feed-throughs in each electrode cell only require two pins for power and commands, and one more for each electrode. An additional wire could be added to the bus for communications. Any type of wire able to carry data could be used, for instance an optical fibre.

The power signals in each wire may be switched at the same time to maintain them in opposite phase. The amplitude of each power signal may be in the range of 5 to 10 volts, and typically one of the signals will be at 0 V while the other will be at the amplitude voltage. The ground datum is the negative supply of the implant controller.

Stimuli may be delivered in the form of biphasic pulses which have an anodic and a cathodic phase, with matched charge in each phase.

The control logic of each electrode cell may recover timing information from at least one of the power signals to coordinate a selected electrode to step through anodic and cathodic phases of the biphasic pulse in cooperation with at least one other electrode.

The timing information may be in the form of power crossovers in the power signals. Advantageously, this allows crossovers to carry information. The power crossovers may have fixed crossover frequency. Oscillators in the implant controller may be used when sending data to electrode cells. And, oscillators in the electrode cells may be used when sending data to the implant controller.

The commands may define the amplitude and the width of each phase the biphasic pulse and whether the biphasic pulse is cathodic or anodic in the first phase. Although biphasic pulses are commonly used, monophasic pulses, or pulses having any arbitrary shape could be defined.

The commands may also be used to coordinate telemetry measurements. In this case, the recovered commands may select plural electrodes to make telemetry measurements. The selected electrodes may make measurements in sequence and deliver telemetry measurements to the implant controller.

The control logic in the implant controller or electrode cells, or both, may be provided by a processor or programmable logic array. However, smaller solutions are preferred, for instance involving state machines or simple logic arrays or VLSI chips. The implant controller may have a reference electrode, which in use is in contact with the tissue. The electrode cells may be very small to enable their use in confined spaces, such as the cochlear or spine. Stimulus selectivity may be controlled by increasing the density of electrodes.

Another advantage of the power signals is that the system may continue to operate safely after a single fault failure, that is, where one of the wires has its insulation breached.

The electrodes will generally be powered to deliver stimuli while the power signals are steady, and stimulation will cease during the periods of switching, when the power signals crossover.

Commands may be modulated onto at least one of the power signals using phase modulated pulse pairs. The implant controller and electrode cells may each comprise a switch to selectively allow the flow of stimulus current from the implant controller to the electrode cell, and vice versa, or between electrode cells, and to control the direction of stimulus current.

The command signals modulated onto the power signals may comprise a combined clock and data signal. The clock signal may be represented by a waveform having regular rising and falling edges, data may be coded by changes in the duty cycle of the clock waveform. These data signals could be defined as a voltage across the two wires, typically about 0.1 volts or less. Such clock and data signals may be recovered from the clock signals after reception by the use of analogue or digital logic decoders.

The communications protocol for carrying data and timing information over the two wire bus may trade noise immunity for power. Data signals may be sent using small signal excursions that have low power but subject to interference. More sensitive information, such as timing information, may be sent using the larger voltage crossover events that are much more immune to interference. Every data signal may be echoed back to the implant controller for verification of delivery.

The electrode cells may be able to store commands for more than one stimulation. Also, more than two of the electrode cells may take part in generating a stimulus.

In a second aspect, the invention is an implantable implant controller for delivering neuro-stimulation, including control logic to transmit two time-varying power signals, varying between two levels and out of phase with the other, and to modulate a command signal onto at least one of the power signals; wherein, in operation, the implant controller is connectable to plural electrode cells via a two-wire bus, the bus being operable to carry a respective one of the time varying signals in each of the two wires, and to carry the command signal, and each electrode cell having control logic to extract charge from the power signals and recover commands from the command signal.

The controller may further comprise a reference electrode and a multi-pole switch to selectively connect the reference electrode to a voltage source, a current source or an open circuit to coordinate delivery of the stimulus.

The controller may further comprise a control logic and an alternator to deliver the two time varying power signals, each varying between two levels and each being out of phase with the other, and a clock and data transmitter to modulate the power signals with clock and data signals.

In a third aspect, the invention is an implantable electrode cell for delivering neuro-stimulation, including: at least one electrode; and control logic to extract charge from two time-varying power signals, varying between two levels and out of phase with the other, to recover commands from a command signal modulated onto at least one of the power signals, and to deliver extracted charge to the electrode; wherein the electrode cell is connectable to an implant controller and at least one other electrode cells via a two-wire bus, the implant controller having control logic to transmit the two time-varying power signals and the command signal, and the bus is operable to carry a respective one of the time varying signals in each of the two wires, and to carry the command signal.

In operation, when recovered commands select an electrode of the electrode cell to deliver a stimulus, the control logic within the selected cell may use the commands to control the selected electrode to deliver extracted charge, in cooperation with at least one other electrode.

The electrode cell may further comprise a multi-pole switch to selectively connect an electrode to a voltage source, a current source or an open circuit to coordinate delivery of a stimulus. One pole of the multiple switch may connect the electrode to a voltage source, another to a current source and another may leave the electrode disconnected. Typically the control logic of the electrode cell will decode commands to selectively control the connection of an electrode cell to a voltage source, a current source or to a disconnected state.

It is generally preferred for the control logic in each electrode cell to be housed in a chip no more than 1 mm long by 0.5 mm wide. Large electronic components, such as external supply bypass capacitors, discrete rectifier diodes or reference crystals for clock generation are not necessary in the design, and are avoided. The control logic may be implemented on a silicon or silicon-on-sapphire chip, which may provide a substrate for mounting any other components should they be required.

Other components may include an on-chip rectifier and storage capacitor to extract charge from the power signals; a clock and data receiver to recover clock and data signals; and a current source to deliver extracted charge to an electrode.

It should be noted that the electrode cells do not use free-running clocks that consume power when there is no activity. This means selected cells, or even the entire array, can be shut down by removing power; making it fail-safe. In the electrode cells the power consumption of the control logic is proportional to the data rate. Another advantage is that decoding at the cells is insensitive to process variations over a 10:1 range; unlike coding schemes, such as Manchester coding, that require a clock in the receiver.

The plural electrode cells may each have control logic, at least one tissue stimulating electrode, a rectifier to extract charge from the power waveforms, a decoder to recover the clock and data signals, and a crossover detector to extract system timing information.

In a fourth aspect, the invention is a method of operating an implantable electrode cell for delivering neuro-stimulation, comprising the steps of receiving two time-varying power signals varying between two levels and out of phase with the other, and a command signal modulated onto at least one of the power signals; determining whether the signals are addressed to the electrode cell; if the electrode cell has more than one electrode, determining which electrode is selected; directing electrical charge from the signals to an on-board current source, then recovering commands from the command signal and setting the current of the current source to the value defined by the recovered commands. Connecting the electrode to the on-board current source at a first time prescribed by the recovered commands. and, disconnecting the electrode from the current source at a second time prescribed by the recovered commands.

In a fifth aspect, the invention is a pair of signals for transmission between an implant controller and an electrode cell, comprising: Two time-varying power signals, each varying between two levels and each being out of phase with the other. Wherein at least one of the power signals is modulated with commands. Wherein, the command selects an electrode of at least one of the electrode cells to deliver a stimulus. And wherein, the control logic within the selected cell uses the command to control the selected electrode to deliver charge extracted from the power signals, in cooperation with at least one other electrode.

Commands may be modulated onto the power signals using differential pulse position modulation, pulse phase encoding, or a variety of other encoding schemes.

In a sixth aspect the invention is a distributed implantable neuro-stimulation system, comprising an implant controller; one or more electrode cells; and a bus interconnecting the implant controller and the electrode cells, to carry power and command signals; wherein there are 'n' wires in the bus and 'm' electrodes and $1 < n < m$.

BRIEF DESCRIPTION OF THE DRAWINGS

The exact nature of this invention, as well as the objects and advantages thereof, will become readily apparent from consideration of the following specification in conjunction with the accompanying drawings in which like reference numerals designate like parts throughout the figures thereof and wherein:

FIG. 13 is an impedance circuit that is equivalent to the combination of a controller and multiple electrode cells; and FIG. 14 is a diagram of a link layer frame.

DETAILED DESCRIPTION OF THE PREFERRED EMBODIMENTS

Figure 1:
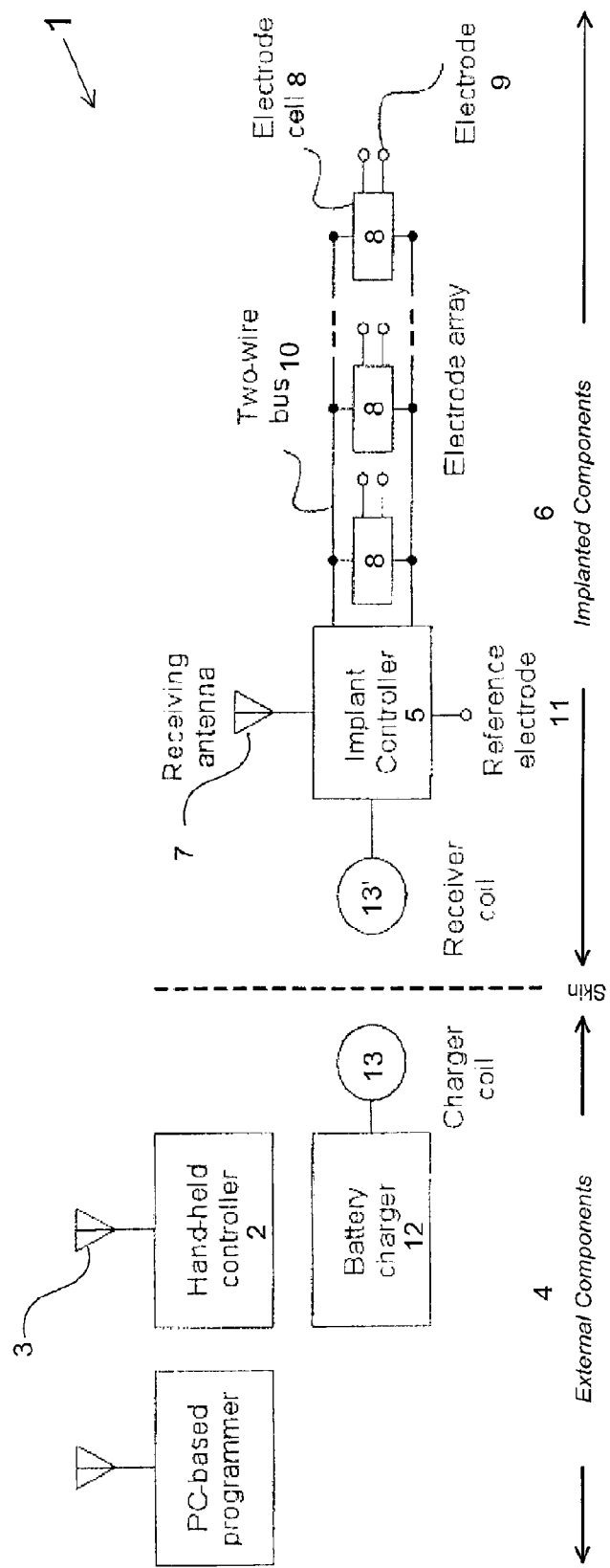
FIG. 1 is a block diagram of the implant architecture.

Referring first to FIG. 1, the implant architecture 1 comprises an external PC based programmer and hand-held controller 2 and a transmitter 3, located outside the body 4. The transmitter 3 communicates with a distributed implantable neuro-stimulation system comprising an implant controller 5, plural electrode cells 8 and an interconnecting two-wire bus 10 in the body 6. The implant controller 5 has a receiver 7 to receive communications from transmitter 3. In general each of the electrode cells 8 has one or more stimulus electrodes 9, and all the electrode cells 8 are connected to the two-wire bus 10 in an identical manner. The two-wire bus 10 is connected back to the implant controller 5. The implant controller also has a reference electrode 11. A battery charger 12 recharges the battery in the implant controller 5 via a charger coil 13 and receiver coil 13'.

In general the implant controller 5 and electrode cells 8 have a sealed exterior wall to isolate the interior electronics from the body tissues and fluids. The electrodes 9 and the bus 10 require access through the wall, and a feed-through 15 is provided in the wall for this purpose; seen in FIG. 3. The feed-through maintains the seal in the wall but provides individual electrical pathways through the wall for both conductors 14 and 16 of the bus 10 and the electrodes 9, 11.

In use, the one or more electrodes 9 of each electrode cell 8 and the reference electrode 11 of the implant controller 5 are required to deliver electrical stimuli according to a predetermined pattern. A continuous direct current (DC) can generate harmful compounds and ions in animal tissues, so each electrical stimulus is generally in the form of biphasic stimulation pulses that may vary in amplitude, duration and separation. For a full discussion of the actively and passively balanced waveforms that are suitable, see Donaldson, N. de N. and Donaldson, P. E. K. (1986) 1. *Historical background; Pt resting potential, Q studies*, and 2. *pH changes; noxious products; electrode corrosion; discussion*, both of which are incorporated herein by reference.

Figure 3:
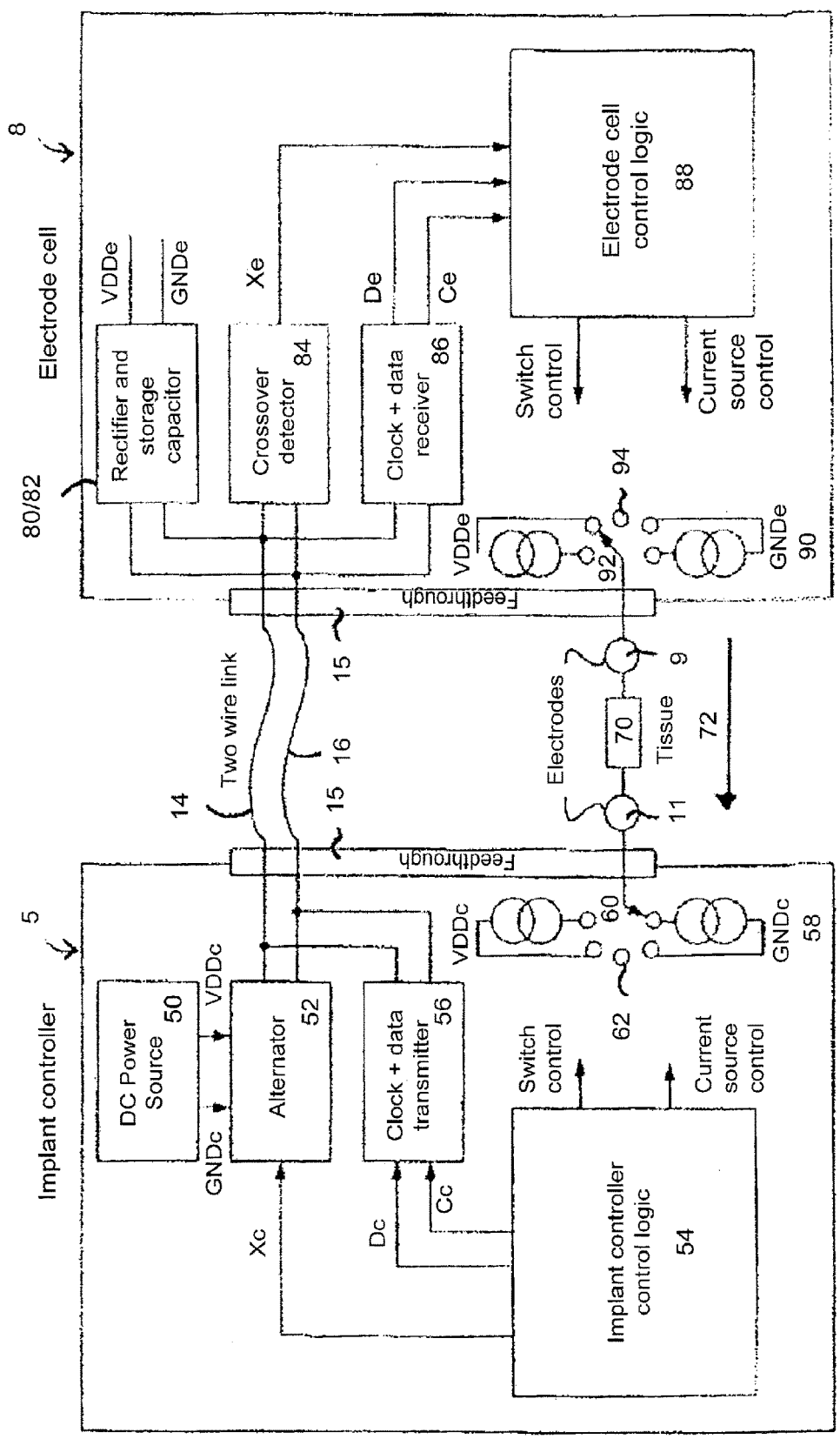
FIG. 3 is a functional block diagram of an implant controller and an electrode cell, showing the connections between them.

During tissue stimulation the electrical circuit starts at a transmitting electrode 9 of an electrode cell 8, passes into the tissue requiring stimulation and through the body to a receiving electrode; seen in FIG. 3. The receiving electrode may be another electrode of the same cell, an electrode of another cell, the reference electrode 11 of the implant controller 5, or any combination of these. The two wire bus 10 completes the circuit.

Hardware

The implant controller 5 is usually the system master, and all the electrodes cells 8 are slaves. Each electrode cell 8 has a unique physical address on bus 10 so that commands can be directed explicitly to each cell 8. The address is programmed into each electrode cell 8 where it is stored; for instance in some kind of non-volatile memory, laser trimming, EEPROM, fused links or any other convenient method.

Where a cell 8 has more than one electrode, each electrode will have a unique physical address; being a unique electrode channel number. Two or more electrodes may be combined under one electrode channel number forming one addressable unit (AU). Each electrode may also be connected to multiple AUs.

Figure 2:
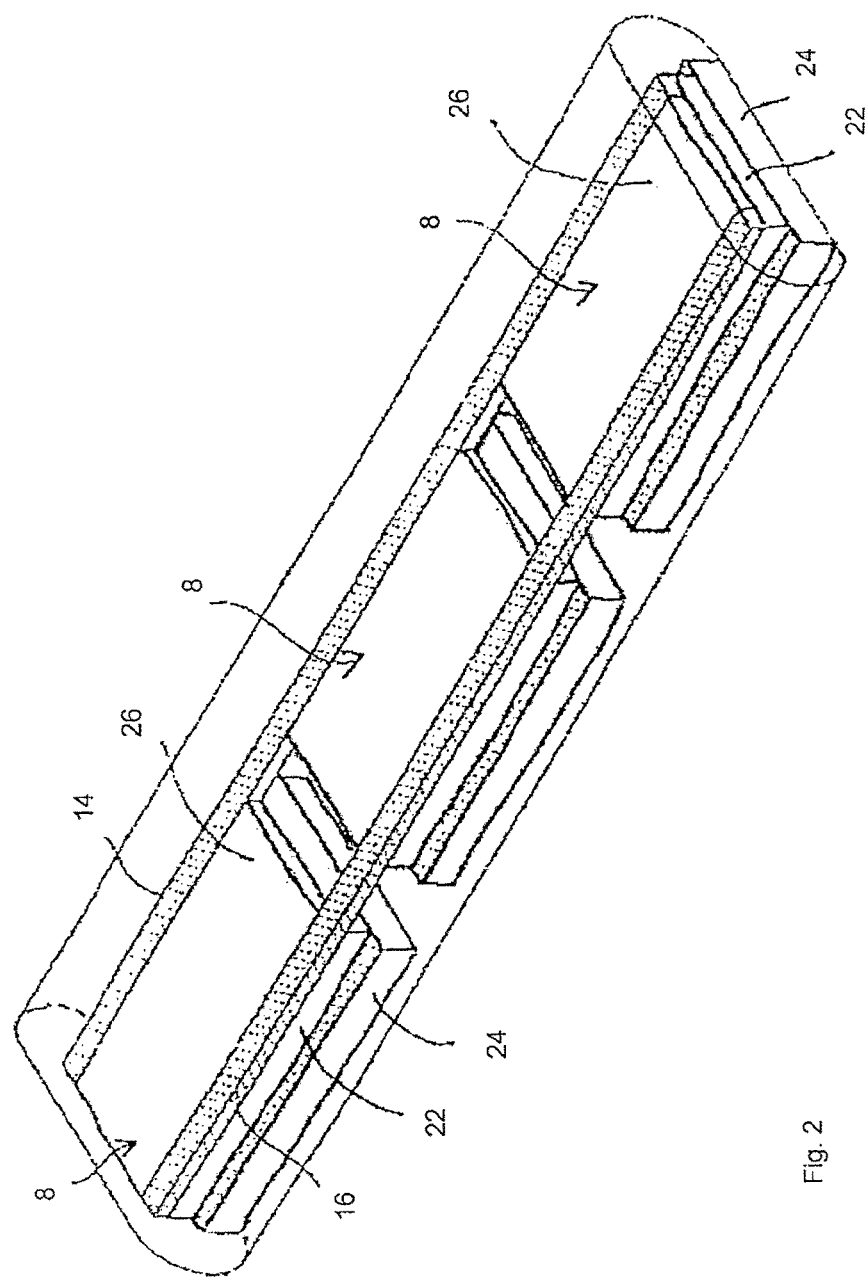
FIG. 2 is a schematic diagram of the mechanical implementation of an electrode cell.

The mechanical arrangement of an electrode cell 8 is shown in FIG. 2. The two wires 14 and 16 of the bus 10 connect to a bond pad 22 on the surface of substrate 24. These bond pads 22 are also connected to an integrated circuit 26 that is mounted on top of it and hermetically sealed.

Referring now to FIG. 3, the main components of an implant controller 5 and an electrode cell 8 will be described.

Implant Controller 5

First, implant controller 5 is seen to house a DC power source 50 that powers the entire implanted system 6 at voltage VDDc. This is typically a rechargeable battery that is charged via an inductive link from outside the body.

An alternator 52 converts the DC signal VDDc from the battery 50 into a time varying power signal that can safely be sent to the electrode cell 8 over the two wire link 10. This prevents exposure of any tissue to continuous DC signal even in the event that the insulation fails. The alternator 52 is controlled by the signal Xc received from the implant controller control logic chip 54.

The clock and data transmitter 56 is controlled by clock signals Cc, and data signals Dc received from the implant controller control logic chip 54. It operates to superimpose a combined data and clock signal on both wires 14 and 16 of the bus 10. The implant controller control logic chip 54 also provides control outputs to the current source 58 in the implant controller 5, and to a multi-pole switch 60.

Electrode Cell 8

At the electrode cell 8 a set of corresponding components receive the signals transmitted from the implant controller over bus 10 and perform the converse functions to those of the implant controller 5.

A full wave rectifier 80 and capacitor 82 converts the power signals received over bus 10 to a local electrode cell supply defined by VDDe and GNDe. Provided there are no losses in the rectifier 80 VDDe will be identical to VDDc. U.S. Pat. No. 4,533,988 (Money and Daly) provides a good example of a suitable active bridge rectifier for this purpose and is incorporated herein by reference. The capacitor 82 not only smoothes the output but also provides continuity of output during the power signal crossovers 110; see FIG. 4. Each crossover 110 may extend for ~100 nS. For an electrode cell 8 current consumption of 10 μA, and allowing 1V droop during the crossover, a 1 pF capacitor 82 is required. This can be easily built in a small area using integrated circuit technology.

A crossover detector 84 detects zero-crossings in the power signals received on bus 10 to regenerate a timing signal which is the analog of Xc, and is called "Xe" when in the electrode cell. This signal is then available to be used for stimulation control. The clock and data receiver 86 extracts data De and a clock signal Ce that correspond to the data Dc and clock Cc signals in the implant controller 5. The timing Xe, data De and clock Ce signals are received by an electrode cell control logic chip 88 and used to control an on-board current source 90 and a multi-pole switch 92.

By coordinating the implant controller 5 and one or more electrode cells 8 it is possible to generate biphasic stimulation pulses, to stimulate the surrounding tissues 70.

Tissue Stimulation

A charge-balanced biphasic pulse is generated using the electrodes, switches and current sources in the implant controller 5 and electrode cell 8. Referring further to FIG. 3, when the multi-pole switch 60 in the implant controller 5 is in the position shown (connecting the reference electrode 11 to VDDe) and the multi-pole switch 92 in an electrode cell 8 is connected to VDDe, then a controlled current stimulus flows from the electrode cell to the implant controller 5 via the tissue 70 and the reference electrode 11; in the direction of arrow 72.

No current flows when the switches in both controller 5 and cell 8 are connected to the respective unlabelled terminals 62 and 94. And, a controlled current stimulus flows from the implant controller 5 to the electrode cell 8 via the tissue 70 and electrode 9 when the switch 60 in the implant controller 5 connects the reference electrode 11 to VDDc, and the switch 92 in the electrode cell 8 connects electrode 9 to the current source GNDe 90. The stimulus current is typically in the range 100 uA to 5 mA.

When switch 60 is connected to VDDc and switch 92 is connected to VDDe then, provided VDDc and VDDe are identical, the electrodes 9 and 11 are effectively shorted together and no current will flow through them; other than that resulting from charge stored on the electrodes themselves. This is beneficial to the system, as it reduces the amount of chemical by-products generated by the stimulation. This shorting can be achieved using an active full-wave rectifier in the electrode cell, as a diode bridge will cause these voltages to be at a different potential, and this potential may generate harmful chemical products.

To generate a charge-controlled biphasic pulse, the current must be regulated in both phases. Current sources 58 and 90 are shown to be in the implant controller 5 and electrode cell 8 respectively, but it will be appreciated that they could both be located in one or the other.

Power, Clock and Other Data Transmission

Figure 4:
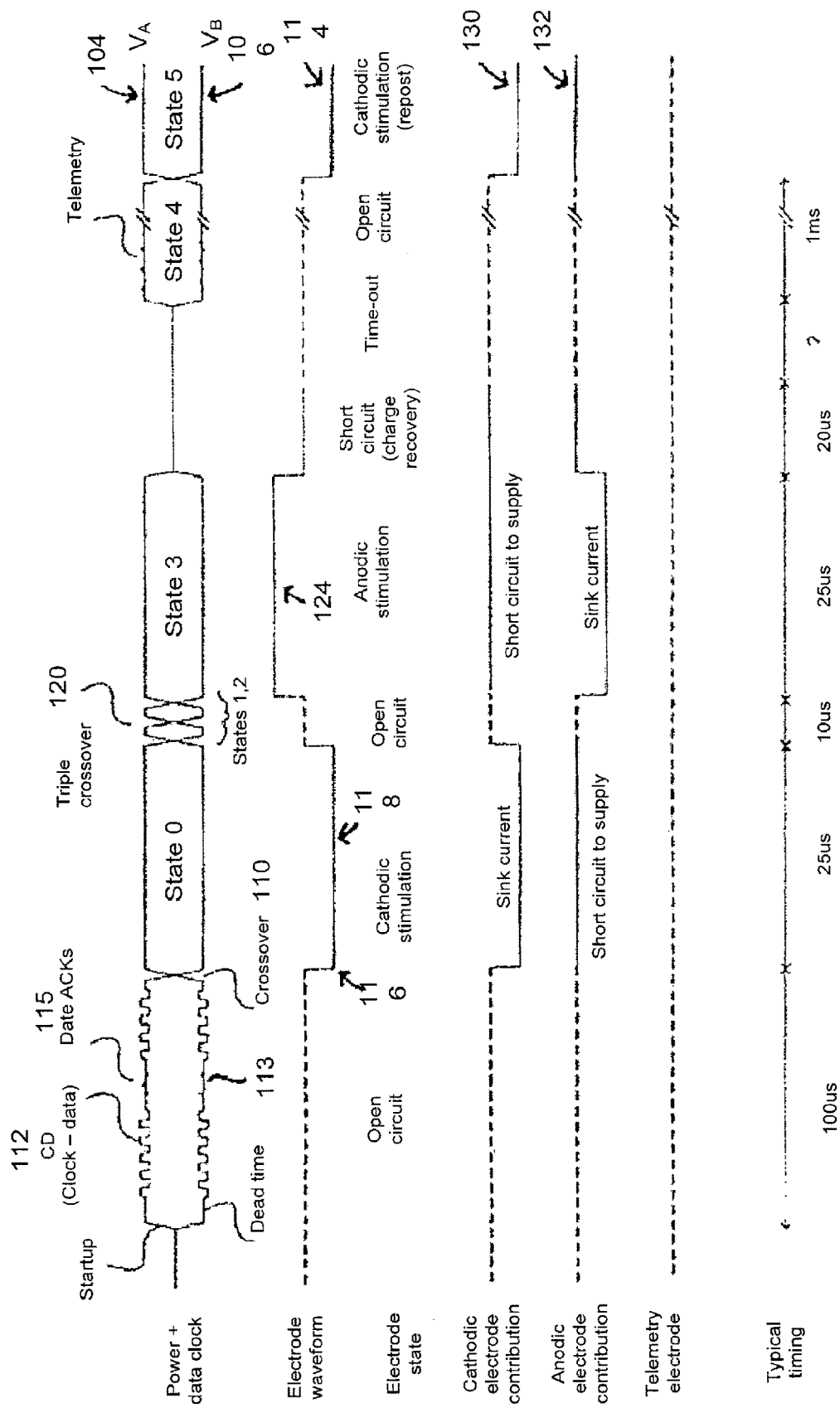
FIG. 4 is a signal diagram showing the signals carried by the two wire link.

FIG. 4 illustrates typical voltage waveforms on the two wire link 10. Initially, the electrode cell 8 has no stored commands. Its power has been removed, and all internal memories have lost their data. All electrodes are open circuit. Power is then applied. After some "dead time", during which analogue circuits in the electrode cells settle, the transmitter starts sending commands, as modulated onto power signal 106, to the cell 8.

The power signals 104 and 106 vary between two levels VA and VB and are out of phase with the other. The power signal 104 seen on conductor 14 rises to voltage VA, then it falls to VB and rises again to VA, and so on. VA is typically between 5 V and 10 V and VB is typically 0 V. The power signal 106 on conductor 16 rises and falls conversely with the voltage on wire 14. These two large amplitude waveforms 104 and 106 on respective conductors 14 and 16, are used to transmit power from the controller 5 to the cells 8.

Since the voltage amplitude on each conductor changes at the same time as the other, there are regular voltage crossings; generally indicated at 110. The crossover 110 typically extends over 10-100 ns depending on the capacitance between the conductors and the output impedance of the alternator 52. This value is not critical, although a shorter period is necessary when the clock or data are transmitted at a higher rate.

The combined clock and data signal 112, is seen as a series of impulses (but is shown in the drawings as small square-waves for clarity) modulated onto a first cycle of the power signal 106, with an amplitude in the order of 0.1 mVpp to 10 mVpp. It takes approximately 50-100 bits of data to specify a command for one electrode cell 8. This starts the cell 8 performing its commands. In the example in FIG. 4, the commands instruct the cell 8 to perform repetitive stimulation. All other cells that are not programmed disable their receivers.

The biphasic stimulus is generated by different cells 8 on the array coordinating their current-source and short-to-supply activities. A resulting biphasic stimulus signal 114 is also shown in FIG. 4 to illustrate the timing relationship. This signal begins at time 116 in the second cycle of the power signals, after crossover 110, with a long negative (cathodic) stimulation 118 that ceases before the next crossover 120. During the third cycle of the power signals, between crossover 120 and the next crossover 122, there is a long positive (anodic) stimulation 124. Note that no stimulation occurs during the crossovers because there is insufficient power.

Figure 5:
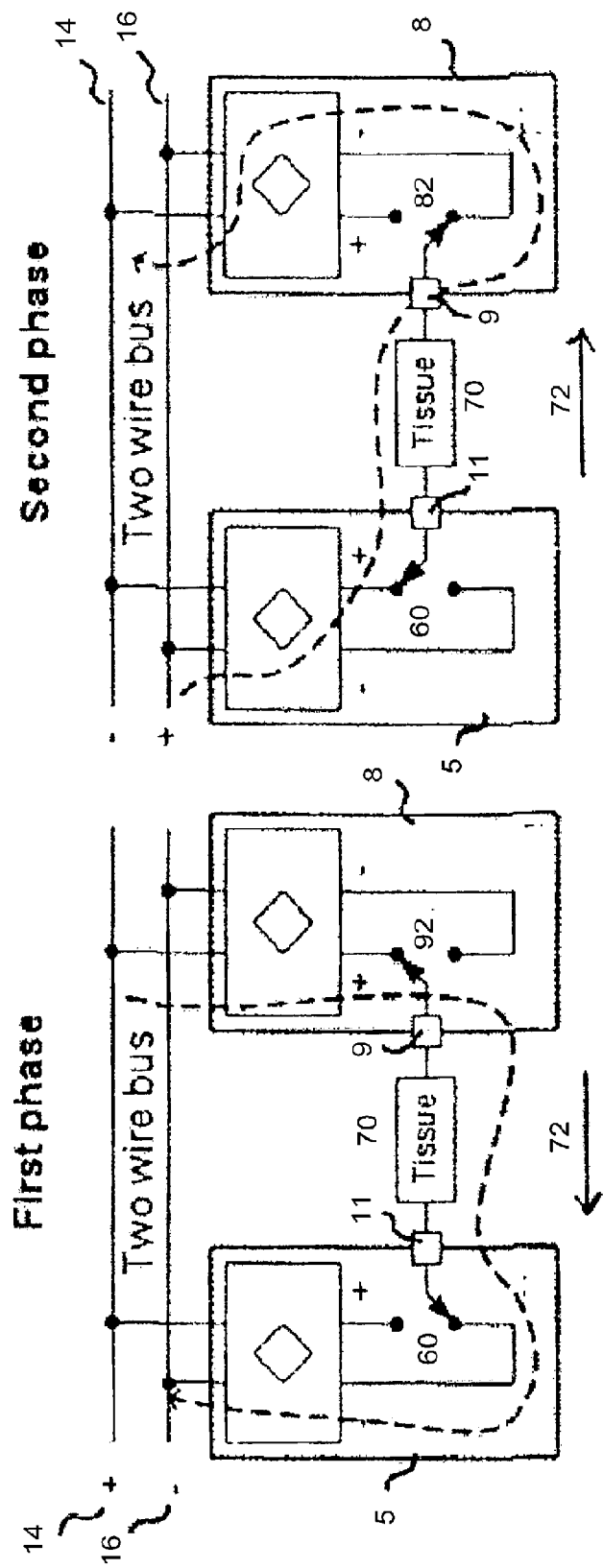
FIG. 5 is a circuit diagram showing the direction of current flow in a first and second phase of a biphasic pulse.

The traces for "cathodic electrode" 130 and "anodic electrode" 132 in FIG. 4 show what would be measured at the output of each electrode cell 8 on its own. While they are working in circuit with each other, the waveforms would match the stimulus. The corresponding current flow between the cathodic and anodic electrodes is shown in FIG. 5. In the first phase, current flows from the electrode cell 8 to the implant controller 5 via electrodes 9 and 11 in the direction of arrow 72 to create a cathodic stimulus. When polarity of the time-varying signals on the two wire bus 14 and 16 is reversed in the second phase, the direction of the current is reversed, creating an anodic stimulus.

Following the stimulus, the two electrodes are shorted together; the system relies on active rectifiers that have small voltage drop between the electrode and the bus, so electrodes can be shorted together for charge recovery. The shorting period works in two steps. Firstly, the bus is shorted together by the implant controller 5, while the electrode cell 8 shorts the electrodes to one or other of the power lines. This state lasts until some timeout in the electrode cell 8 has ended, and which point the electrode cell and implant controller remove the electrode-to-supply shorts. After some further time the implant controller 5 then reapplies the power.

Referring to FIG. 4 again, there is a triple crossover 120 at the inter-phase gap to provide an inter-phase gap while keeping signal on the two wires 14 and 16 DC-free. A double crossover (providing time for an inter-phase gap) causes the supplies to have the same polarity for the first and second stimulus phases and thus a net DC voltage. The triple crossover reverses them and eliminates this DC.

Stimuli can also be repeated without reprogramming. The parameters for repetition are recovered from the commands modulated onto the power signals and stored by the electrode cell 8. An electrode cell 8 can potentially store more than one command. A command sequence can be restarted by restarting the electrode cell counters when they reach the period of repeating.

If an electrode cell receives a corrupt command the electrode cell is set into an unknown state, which may result in serious complications. However, for complexity reasons no error checking or message retry mechanism is implemented in the electrode cells. In order to ensure correct transmission each command is echoed by the electrode cell back to the controller. If the data received by the controller is different to the transmitted data, the implant controller resets the array and restarts the programming of the array.

Programming is performed without a crossover until all data has been sent and checked. The first crossover after a programming session causes all electrode cells to disable their data receivers in order to preserve the power of functions which are no longer needed.

Electrode cells that have not been programmed enter a low-power state in which they remain until they are reset by having their power removed. The implant controller holds the bus in a constant state opposite to the state during programming for a time equal to that used for programming in order to avoid net DC on the two-wire bus.

The implant controller advances the electrode array through its states using crossovers and power shorting. A "program" consists of repetitive stimuli on two or more electrodes. Two or more electrodes stimulate at the same time. These can be in one or more electrode cells.

There can be multiple programs operating at once; this allows electrodes to provide non-overlapping stimuli. A stimulus has multiple phases that are generated by clocking the implant through its states as illustrated in FIG. 4: 1. The first phase of the stimulus occurs when the implant is in state 0. 2. The inter-phase gap of the stimulus occurs while the implant is clocked through states 1 and 2. Two states are used to ensure the bus voltage is DC-free. 3. The second stimulation phase occurs while the implant is in state 3. 4. During the transition from states 3 to 4, the bus is shorted to allow charge recovery. This is followed by a period when the electrodes and the bus are open circuited. The electrode cells use internal counters to time their shorting periods; the open circuit period allows for manufacturing variation between the electrode cells and implant controller and prevents a race condition when power is reapplied to the bus. 5. State 4 begins at the end of the shorting period when power is re-applied to the bus. 6. States 4 and 5 are used to set the stimulation rate. Two phases are used to ensure the bus voltage is DC free. All states can be used for telemetry, although a crossover will overload the data receivers for ~20 μs, creating a period during which communications ceases.

Figure 6:
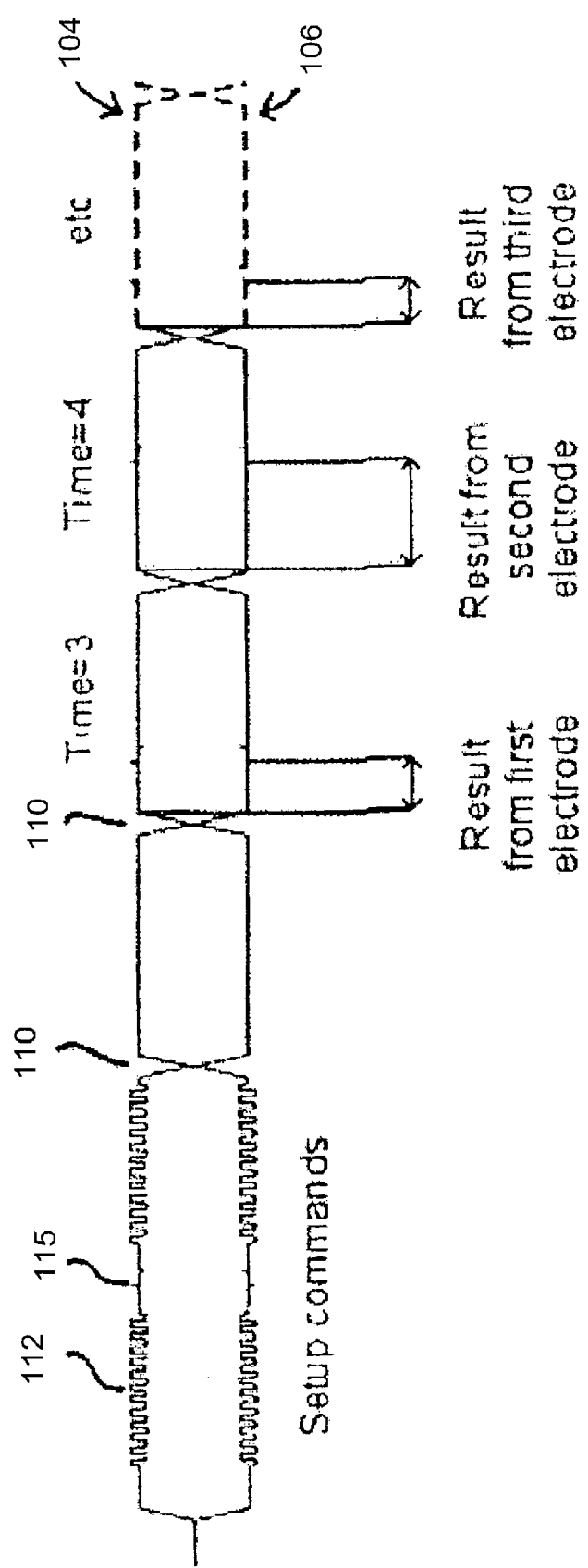
FIG. 6 is a signal diagram showing timing for telemetry measurements and delivery by plural electrodes.

FIG. 6 shows voltage waveforms on the two wire bus 10 when three electrodes are instructed to perform telemetry. Once the setup is complete, the bus 10 is used purely for telemetry data. There is no need to continue to instruct electrodes. Every electrode 9 has a different delay, so they take turns to make their measurement and to transmit results to the implant controller 5. As shown, the electrodes take turn to transmit results to the implant controller 5. Advantageously, this makes better use of the communications bandwidth available on the bus.

Charge Balance

Figure 7:
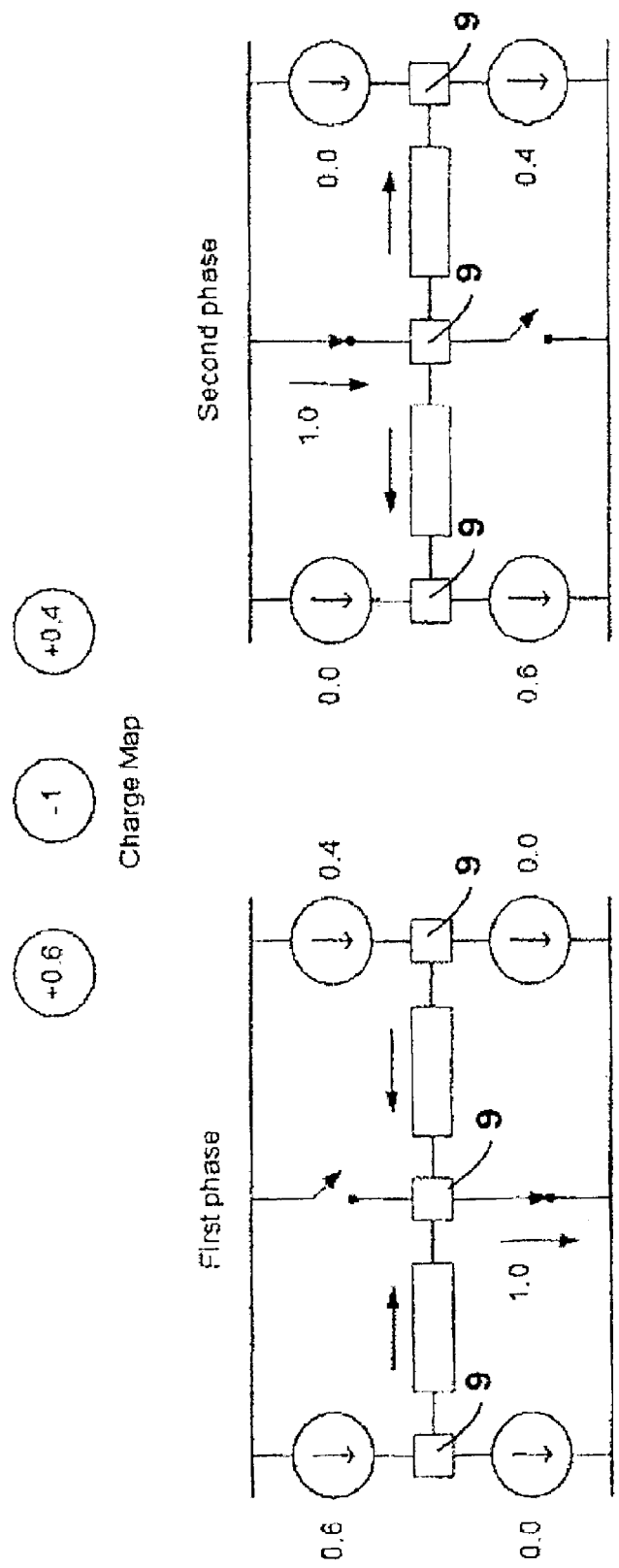
FIG. 7 is a circuit diagram showing current source matching when three electrodes are used.

FIG. 7 shows an example where three electrodes 9 are selected to perform current steering. The charge is shown to be balanced at each electrode, even though the current sources of the individual electrodes are not matched. For example, if the right and left side electrodes had been programmed to deliver 0.5 units, then the error of them providing +0.6 and +0.4 units does not affect charge balance. This is beneficial, as means that for balanced stimulation, it is not necessary during manufacture to accurately match the current drivers of different electrode cells, but only within a given electrode driver.

To achieve charge balance, it is only necessary that the sum of currents flowing into the tissue matches the sum of currents flowing out of the tissue. As shown in the corresponding charge map in FIG. 7, the positive changes +0.4 and +0.6 of the left and right electrodes balance against negative charge −1 of the middle electrode.

Figure 8:
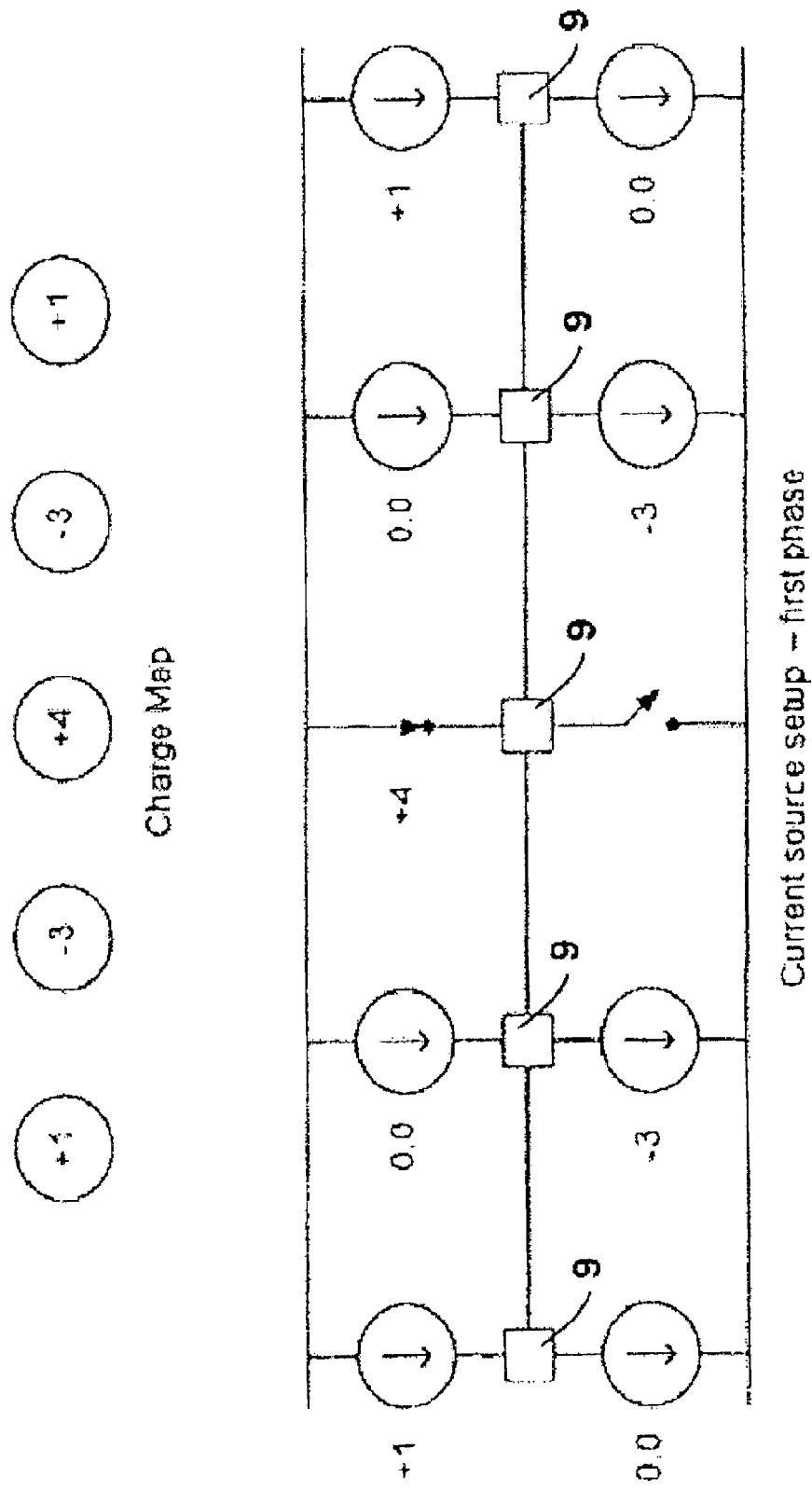
FIG. 8 is a circuit diagram showing current source matching when five electrodes are used to perform current steering.

Similarly in FIG. 8, a more complex steering is performed by five electrodes. As shown in the corresponding charge map, the total charge is balanced, in that the positive charges of +1, +4 and +1 of the leftmost, middle and rightmost electrodes respectively balance against negative charges −3 and −3 of the remaining two electrodes.

Electrode Synchronization

There are two counters in the electrode cells and the implant controller that control the operation of the system: the program counters and the state counters. These counters run in lockstep and are incremented on crossovers.

Figure 9:
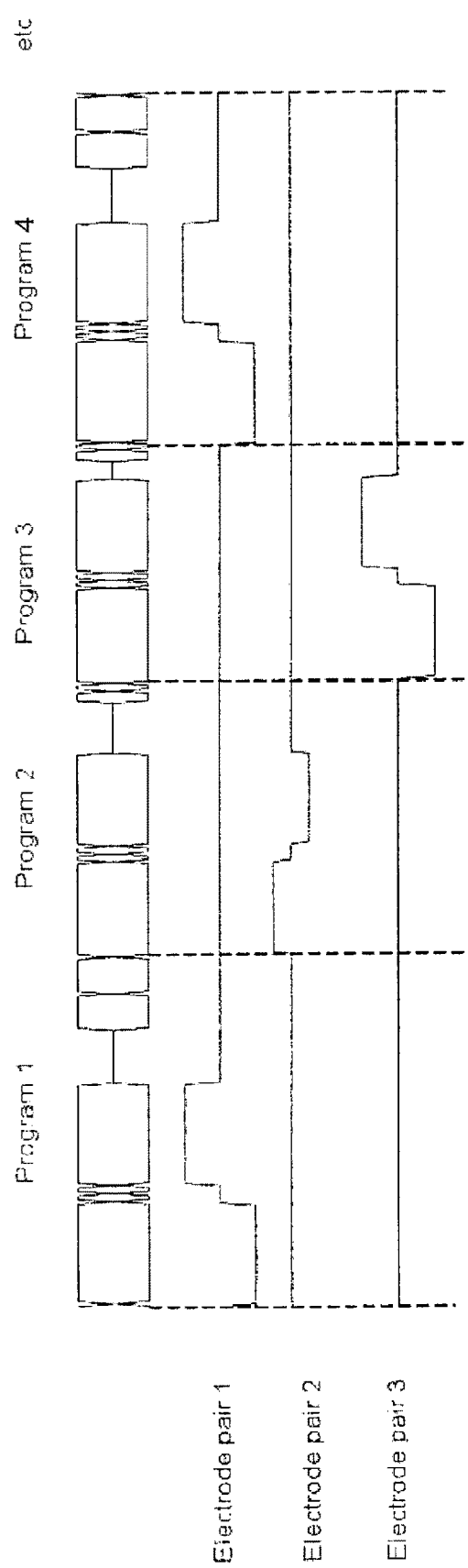
FIG. 9 is a signal diagram showing the signals carried by the two wire link where there are multiple programs.

Both the state and program counters are modular. Each state counter has three bits and counts through six states. The length of the program counters is arbitrary and depends on the number of programs needed for a particular application. In this example, the program counter is two bits long and therefore encodes four programs. A "wrap" parameter sets the modulus of a program counter. Each AU can have its own wrap value, but in most cases the wrap value of all AUs is the same. A "time" parameter sets the program count at which stimulation occurs for an individual electrode. Electrodes having the same time value stimulate together, and so contribute to one program. AUs having different time values provide non-overlapping stimuli and so provide separate programs. This is illustrated in FIG. 9.

Physical Layer

The following deals with the power characteristics of the system comprising the implant controller and the electrode cells. The main constraint for designing the system is that the power available to the electrode cells is limited because all the power has to be extracted from the power signals. Therefore, it is not practical to implement operational amplifiers (op-amp) with large gain in the electrode cells as such op-amps consume too much power.

Figure 10:
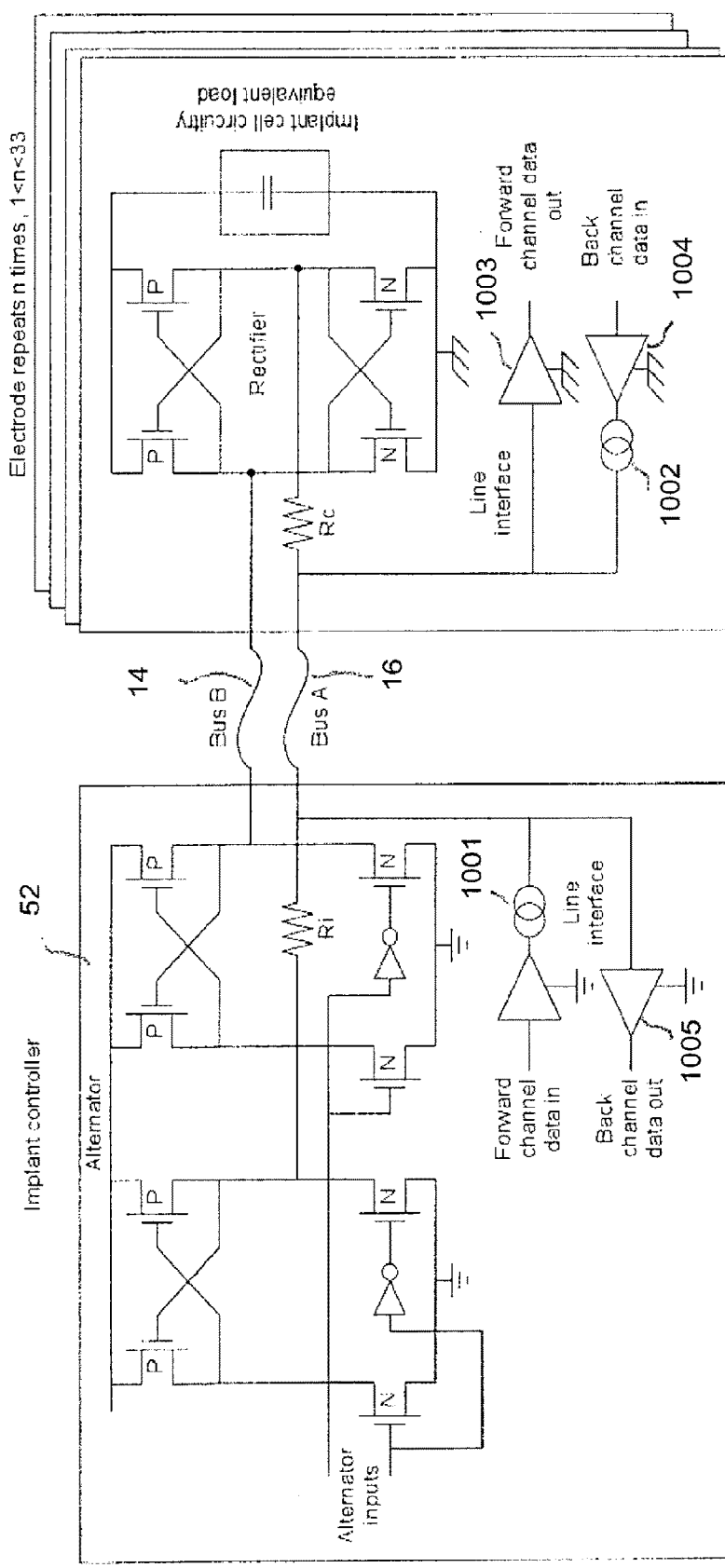
FIG. 10 is a diagram of a controller and electrode cells arranged on a bus that carries both power and data.

The data signals to and from the electrode cells are modulated onto one of the lines 16 of the bus by current sources 1001 and 1002 as shown in FIG. 10. The crossovers to advance the state machines in the electrode cells are generated by alternator 52.

The voltage amplitude of the data signal is limited on the one hand by a maximum voltage of 500 mV peak to peak (pp) to prevent forward biasing the protection diodes in the implant controller. The advantage of operating the bus at the maximum voltage is that less gain is required for receiver amplifier 1003 in the electrode cell. On the other hand, the bus voltage is constrained by the available drive current of the electrode cell drivers 1004 and the impedance of the bus.

Regarding the influence of parasitic effects, it is noted that the bus is largely insensitive to stray capacitance as its impedance is small. For example, a 1 ohm resistance and a 100 pF capacitor produce a time-constant of 100 ps which is much shorter than the time constants of the amplifiers in the receive chain.

The dynamic power dissipation due to switching the power signals connected to a 200 pF load on the two wires over a voltage of 10V with a 1 KHz crossover switching frequency is 10 uW. This indicates an electrode array that is used for 1 hour a day must still be unpowered when not in use.

The amplitude of the signal from the electrode cell to the implant controller could potentially be much smaller than the amplitude of the signal from the implant controller to the electrode cell. This makes use of the fact that a large gain in the controller can be implemented easier than generating a large signal in each electrode cell. However, the input impedance of a receiver op-amp 1003 with small gain is considerably different to the input impedance of a receiver op-amp 1006 with large gain and the result is an impedance mismatch which can be so poor that signal to noise ratio (SNR) becomes an issue. To simplify the overall design an identical link is used for both directions of communication. However, as current signalling is used—in which it is as easy to generate a signal in the implant controller as in the electrode cells, a fully symmetric protocol is being used.

The data rate on the bus in this example is 1 Mbit/s resulting in 50 us to transmit a 50 bit command. The command is echoed back for error detection, which takes another 50 us. This 100 us transmission time has to be matched by an equally long time for charge balancing of 100 us. As a result it takes 200 us to send one command.

The circuitry used to combine power and data is shown in FIG. 10. The bus is asymmetric—the Bus A connection 16 includes a resistor that is absent from Bus B 14. The bus operates in two distinguishable states called "positive," when Bus A 16 has a greater voltage than Bus B 14, and "negative," in the opposite state.

Typically, more than one electrode cell is connected to the bus and the combined input impedance of the electrode cells attenuates the data by a factor proportional to the number of electrode cells. Since there are between 1 and 32 electrode cells in a typical system, the received signal can vary by 16.5:1 including the implant controller. The op-amps in the electrode cells do not require automatic gain control (AGC); the gain setting can be programmed together with the serial number of each electrode cell. If a large number of electrode cells is connected to the bus, the transmit current of the electrode cells needs to be larger in order to drive a larger load. Therefore, the electrode cells have a programmable transmit current, allowing high current to be selected for arrays with large numbers of electrode cells.

Clock and Data Encoding

Data and clock are combined and transmitted on the bus using differential pulse phase modulation. The communication signal contains positive and negative impulses and the sum of these impulses represents a clock signal.

Figure 11:
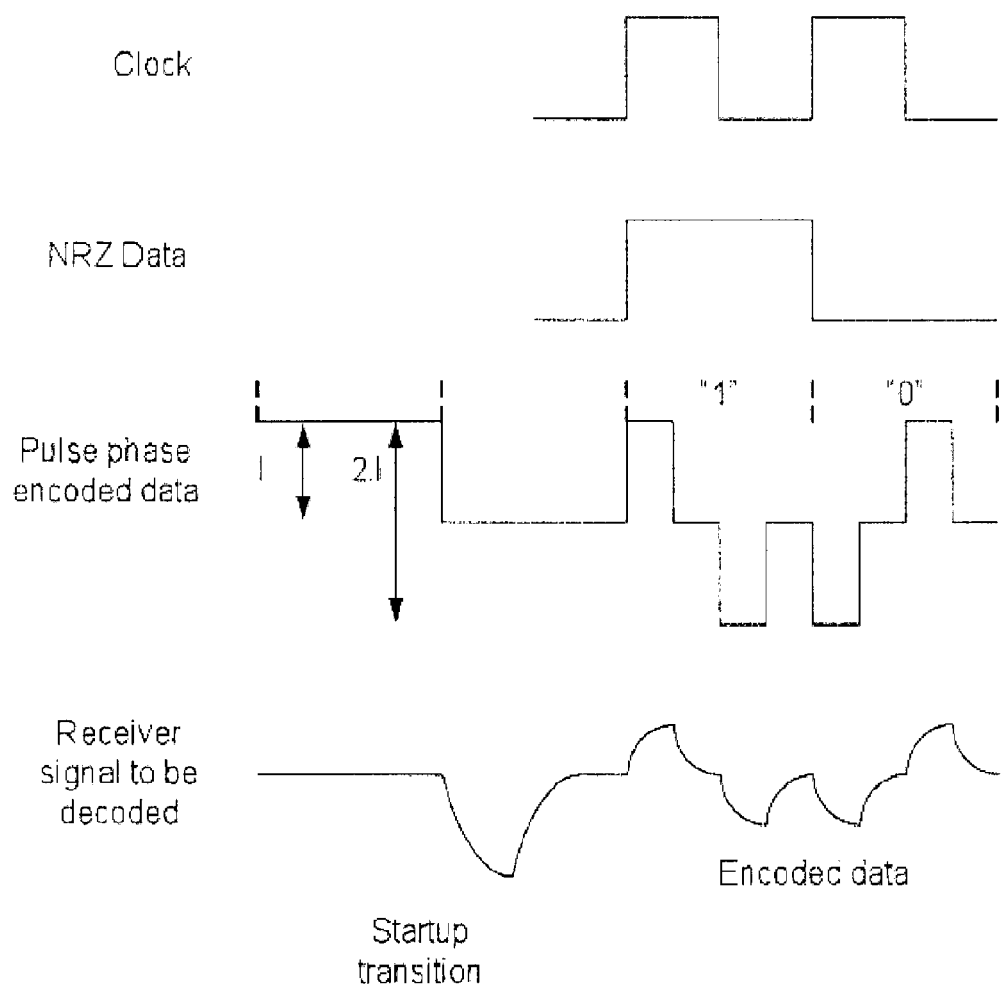
FIG. 11 is a signal diagram showing the components of encoded data and the resulting encoded data signal.

Each bit is represented by a positive and a negative pulse. If the first pulse is positive, the bit value is "1", and if the first pulse is negative, the bit value is "0". The modulation is shown in FIG. 11. Because the current sources can only supply current in one direction but positive and negative pulses are required, the signal on the bus needs to be biased by a bias current before sending data and the receiver output is unpredictable for a time. Enabling the power supply or generating a crossover will also produce a large input to the receiver. The effect of such a large input must have passed before data can be sent. The receiver must be disabled during the startup transition settling time for data to be received correctly.

Figure 12:
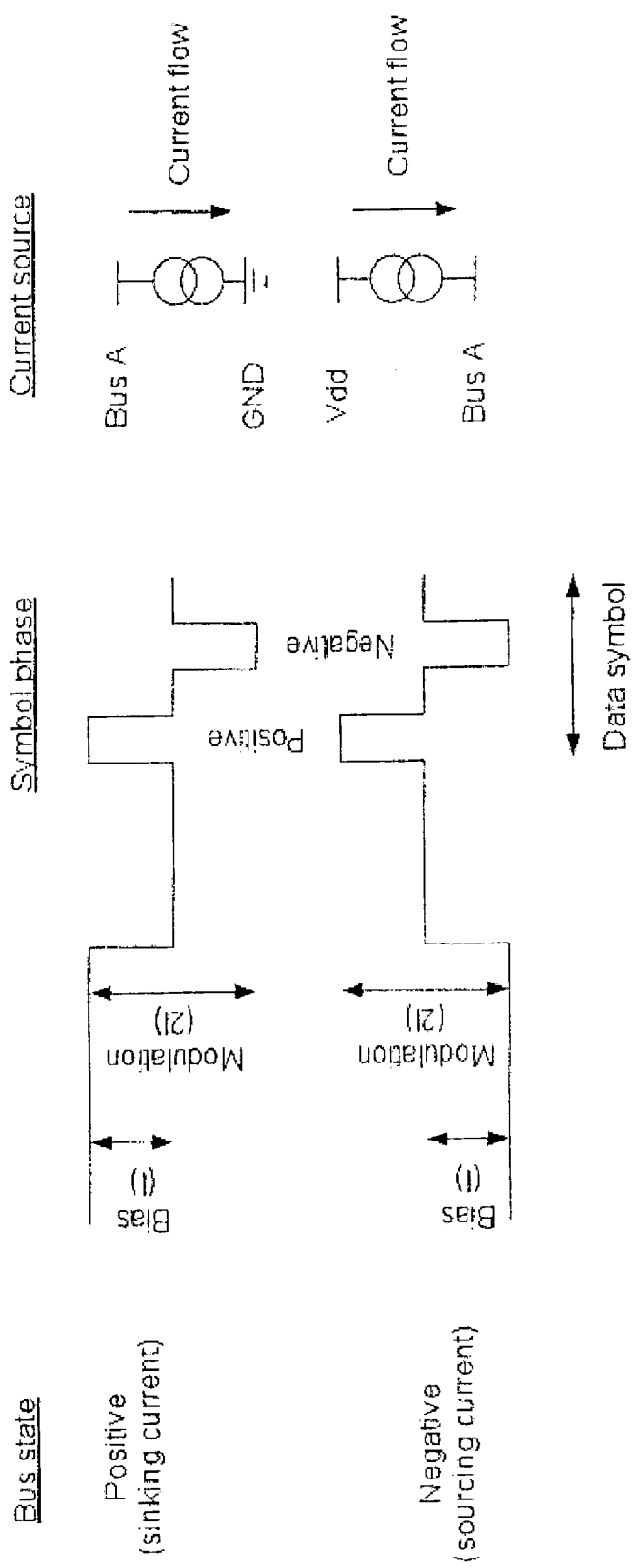
FIG. 12 is a signal diagram showing the effect of positive and negative bus states on the polarity of the bias current and data.

The polarity of the bias current and the data depends on the bus state (i.e. positive or negative) as shown in FIG. 12. Before sending data, the transmitter must establish a bias current. This current flows from the bus to the ground, i.e. is sunk from the bus, when the bus is in its positive state and flows from the supply to the bus, i.e. sourced into the bus, when it is in its negative state. A modulator generates symbols by doubling or disabling this current. The polarity of the data symbols is independent of the bus state, so the state of the bus (positive or negative) affects whether current must be disabled or doubled. For a positive bus state, the current must be disabled for a positive symbol and doubled for a negative symbol and vice versa for a negative bus state. Data is only sent to electrode cells when the bus is in the positive state, whereas telemetry data is sent from the electrode cells to the controller in both bus states. As a result, the data transmitter of the implant controller is simpler than the transmitters in the electrode cells. The receiver is clocked by the data symbol edges and the gap between the positive and negative phases provides time for logic signal propagation.

As mentioned above, it takes 1 us to transmit 1 bit of a command which is divided into four parts: two pulses (one negative and one positive), and two gaps (one after each pulse). As a result, each pulse takes 250 us. When encoded with a fixed data, e.g. 00000 . . . , the spectrum of this signal has peaks at 1, 3, 5 . . . MHz. The spectrum of a single 250 ns pulse has zeros at 2 MHz and 4 MHz. A 4 MHz (−3 dB) bandwidth has been found experimentally to provide acceptable performance.

Clock and Data Decoding

The data receiver consists of an analog interface, demodulator and data buffer. The analog interface generates logic signals ClockP and ClockN from the analog signals on the eLAN bus. The demodulator extracts the clock and serial data from ClockP and ClockN and is part of the ASIC control logic.

The analog interface consists of band-limited amplifier 1003 in FIG. 10 and its output is fed to two comparators. The first comparator has a positive offset and the second comparator has a negative offset. If the signal is above the positive offset, ClockP is asserted, and if it is below the negative offset, ClockN is asserted.

The impedance at 1 MHz presented to the link by an electrode cell circuitry in integrated form is hard to assess; for the purpose of initial designs its internal circuitry is treated as a pure capacitance (the worst-case load), the rectifier is treated as ideal, and resistors were added to achieve the desired performance.

The equivalent circuit to this link used for noise margin calculations is shown in FIG. 13. The resistors Ri and Rc dissipate power during stimulation but provide a load necessary for data link operation—their values are chosen to trade-off these effects. If the resistance is large, the current sources 1001 and 1002 in FIG. 10 need to draw less current to achieve the same signalling voltage or the receiver amplifiers 1003 and 1005 need less gain because the same transmit current results in a larger signalling voltage. On the other hand, if the resistance is small, there is less voltage drop over the resistors and less energy is lost during stimulation. As an example: Rc and Ri are chosen so that there is a drop of 100 mV during a 10 mA single electrode stimulation, i.e. the sum of Rc and Ri is 10 ohms, divided as 9 ohms per cell and 1 ohm in the implant controller. With 32 cells in parallel, they will present an impedance of 0.28 ohms.

If a 1 mA current pulse is chosen to drive the link, it will generate 280 uV. To amplify this to a 3V logic signal requires a gain of 81 dB. This shows the trade-off: a low impedance rectifier provides efficient stimulation; a high impedance rectifier provides efficient data communications. The rectifier could potentially operate in two modes: one for communication, in which it presents high impedance to the bus, and a second in which it has a low impedance to avoid power loss. During electrode voltage telemetry, then usually only a few electrodes will be active at once, so the maximum attenuation situation will not occur.

Telemetry Encoding

Analog telemetry data is communicated using PWM on the back-channel link. The clock rate of the PWM oscillator is nominally 50 KHz. The symbols used are identical to those used for command transmission.

Multiple interleaved telemetry results can be obtained by assigning different program values to the different measurements. Since the link takes ~20 us to settle after each crossover, and it takes 6 crossovers to cycle between programs, the implant can switch between measurements in a minimum time of ~30 us.

Media Access Control

The MAC protocol is as follows: There are two kinds of communications: AU programming and telemetry. The characteristics of AU programming are:

AU programming occurs after a power-on-reset, and at no other time.
Programming starts with a message from the implant controller.
The start of the message contains the length field, and an AU's address.
All cells use the length field to determine the length of the current message, and will use that to determine when the next message will be sent.
Cells only transmit data in response to a command to them from the implant controller.
At the first crossover, all cells disable their data receivers. Cells do not decode telemetry data.

The characteristics of telemetry are:
One cell can send telemetry data at a time.
Cells send data during the selected phase.
Cells do not decode telemetry data.
Cells count crossovers to coordinate activity.

Note that when the link changes state from programming to telemetry, its impedance decreases. This will increase the amplitude of the data signal received by the implant controller. The amplitude varies depending on how many cells remain active. The implant controller adjusts its gain depending on the number of electrode cells active, its dynamic range and the exact circumstances.

Link Layer

Link Layer Format

FIG. 14 illustrates a frame format of the data link layer comprising a length field 1401, an address field 1402, and a data field 1403. The length field 1401 represents the length of the entire frame in bytes. The number of bits for the length field and the address field is also shown in the diagram. 20-bit random numbers are assigned to each AU during manufacturing the electrode cell IC for use as addresses. The relationship between the addresses and the locations of the AUs within the array is stored in an calibration table, which is provided to the implant controller. Each AU address only occurs once within an electrode array. Link layer frames are echoed after they are received and no checksum is provided.

Address Allocation 20-bit random numbers are assigned to AUs for use as addresses. This address size suits a system with 32 randomly selected addresses so the probability of two devices having the same address is less than 0.1%. When a single chip has multiple addresses, collision becomes less likely e.g. with 4 electrode cells, only 17 address bits are needed. But the system design uses 20 to allow for single electrode designs.

Commands

As part of the manufacturing process, the composition of an electrode cell in terms of its AUs should be known. However to safeguard against an error in this information, there are two mechanisms:

1. Ping command—this command allows the contents of each electrode cell to be probed, and will result in a reply that identifies the function of the AU.

2. Command field information—the type of AU being addressed is reflected in the command field; e.g. bit 0 of the command field may distinguish between an electrode and an amplifier module. If the command field does not correspond with the AU type, a NACK is returned to the IC.

| Command Summary | | |
|---|---|---|
| Encoding | Function | Comments |
| 0x0 | Stimulation | |
| 0x1 | Measurement (impedance) | |
| 0x2 | Measurement (differential NRT) | |
| 0x3 | Measurement (single-ended NRT) | |
| 0xF | Ping | |

| Ping | | |
|---|---|---|
| Field Name | Size (bits) | Data Represented |
| Command | 4 | Selects ping command |
| Field size | 4 | The portion of the address that must match for the AU to reply. Encoding TBD |
| Total (Data) | 8 | |
| Total (Frame) | 32 | (Includes 24 bits of link layer) |

| Stimulation | | |
|---|---|---|
| Field Name | Size (bits) | Data Represented |
| Command | 4 | The command. Different commands can use different formats so this allows as many commands as are required |
| Amplitude | 8 | The amplitude of the stimulation for that AU. (Ignored for shorting.) |
| Time | 2 | The time when programmed behaviour is to occur. One time unit is the time it takes for one biphasic pulse |

-continued

Stimulation

| Field Name | Size (bits) | Data Represented |
|---|---|---|
| Wrap | 2 | The parameter used to control repetitive behaviour; the time within a cell is given by count mod wrap where count is the number of crossovers that have occurred since the command was received |
| C/A | 1 | Indicates whether the stimulation is cathodic (sink current) or anodic (source current) in the first phase |
| Short | 1 | Indicates that this AU generates a short circuit to the supplies instead of using the current source. If this is set the "amplitude" value is ignored |
| Shorting period | 4 | Sets the period for which the AU is shorted to the supply after the end of stimulation |
| Total (Data) | 22 | |
| Total (Frame) | 46 | (Includes 24 bits of link layer) |

Measurement

| Field Name | Size (bits) | Data Represented |
|---|---|---|
| Command | 4 | The command. Different commands can use different formats so this allows as many commands as are required |
| Electrode target 1 | 4 | Address of first AU involved in measurement Selects the AU for impedance measurement and either an AU or ground for NRT measurement |
| Electrode target 2 | 4 | Address of second AU involved in NRT measurement (Ignored for impedance measurement.) |
| Time | 2 | The time when programmed behaviour is to occur One time unit is the time it takes for one biphasic pulse |
| Wrap | 2 | The parameter used to control repetitive behaviour the time within a cell is given by count mod wrap where count is the number of crossovers that have occurred since the command was received |
| NRT gain | 3 | Gain choices 60 70 80 90 100 dB Note coding is different for PCB and chip |
| Blanking period | 4 | The blanking time from the end of the shorting period to the time the NRT amplifier is un-blanked |
| Total (Data) | 22 | |
| Total (Frame) | 46 | (Includes 24 bits of link layer) |

Parametric Specifications

TABLE 1

Communications signalling parametric specifications
Data Signaling

| Parameter | Min | Typ | Max | Units | Comments |
|---|---|---|---|---|---|
| Dead time | | 12 | 20 | us | This is the time from the power-up to the start of data communications |
| Data communications drive current | | 1 | | mA | During pause time |
| Communications voltage | 0.25 | | 6 | mVp | 1 mA * 10 Ω\|\| 10 Ω/32 to 1 mA * 10 Ω\|\|10 Ω/32 with additional 20% margin |
| Impedance presented to bus by each cell | | 10 | | ohms | During programming |
| Impedance presented to bus by implant controller | | 10 | | ohms | During programming |
| Positive pulse to negative pulse amplitude mismatch | | 0 | | % | |
| Positive pulse width | | 250 | | ns | |
| Negative pulse width | | 250 | | ns | |
| Time between positive and negative pulses | | 250 | | ns | |
| Delay between crossover and data communications | | 20 | | us | |
| Delay between enabling bias current and communications | | 3 | | us | |
| Telemetry oscillator rate | | 50 | | kHz | |

TABLE 2

Data transmitter analog interface parametric specifications

| Parameter | Min | Typ | Max | Units | Comments |
|---|---|---|---|---|---|
| Minimum bias current | | | 0.5 | mA | |
| Maximum bias current | | | 2 | | |
| Bias current step ratio | | 2 | | | i.e. 0.5 mA 1 mA 2 mA 4 mA |
| Charge mismatch for positive and negative parts of data symbol | | | 20 | % | This is the sum of the errors in current doubling and those of propagation |

TABLE 3

Data receiver analog specifications

| Parameter | Min | Typ | Max | Units | Comments |
|---|---|---|---|---|---|
| HP pole frequency (P1 P2) | | 100 | | kHz | |
| LP pole frequency (P3) | | 2 | | MHz | |
| Offset voltage | | 0.25 | | mV | Input referred |
| Input impedance | 10 | | | kΩ | |

Power Supply Signalling (Crossovers)

TABLE 4

Crossover parametric specifications

| Parameter | Min | Typ | Max | Units | Comments |
|---|---|---|---|---|---|
| Shorting time for charge recovery (no reset) | | 10 | | us | |
| Bus unpowered time during normal operation | | | 100 | us | |
| Shorting time indicating reset | 10 | | | ms | |
| Crossover time | | | 1 | us | 10% to 90% |
| Time between crossovers | 2 | | | us | 90% to 90% |
| Time to enable shorting | | | 1 | us | 10% to 90% |
| Programmable shorting time increment | 2 | 4 | 6 | us | |

Although the implementations described all show just one switch per electrode cell, an electrode cell with multiple electrodes could use its current source to generate a biphasic pulse between two of its electrodes. In this case each electrode could be separately addressable by the controller.

Also, although the specific example has shown all the electrode cells to be identical this is not necessary, and different kinds of electrode cells may be combined in the same system. For instance different kinds of cells may have different numbers of electrodes. Further, a single current source has been described in the implant controller, and in the electrode cell. However, both current sources could be placed in the implant controller so they can be trimmed to match accurately.

Autonomous electrode cells could store a complete set of parameters for a stimulus, or a train of stimuli, or a complete set of commands to do some other function, such as to measure neural potential. They can then generate a complete stimulus in response to a pre-programmed event.

Finally, a third wire may be added to the interconnecting bus 10 to facilitate fault recovery. In one example, one wire can be dropped if a fault develops. Faults are detected by measuring the current into a grounded electrode when the electrode array is not stimulating. If one of the two wires has a fault, the third wire will generate a current when it is driving Vdd and can be detected. In a second example, the third wire is used solely for the purpose of shorting for charge recovery.

What is claimed is:

1. A distributed implantable neuro-stimulation system, comprising:
   an implant controller including two feed-throughs to provide electrical pathways for a first bus signal and a second bus signal, the implant controller further including control logic to transmit a first time-varying power signal and a second time-varying power signal, the first time-varying power signal and the second time-varying power signal varying between two levels, the first time-varying power signal varying in opposite phase to the second time-varying power signal, the first time-varying power signal forming the first bus signal, the second time-varying power signal forming the second bus signal, and to modulate a command signal onto the first time-varying power signal and the second time-varying power signal;
   two or more electrode cells, each electrode cell having two feed-throughs to provide electrical pathways for the first bus signal and the second bus signal;
   control logic to extract charge from at least one of the first bus signal and the second bus signal and recover commands from the first bus signal or the second bus signal; and
   a two-wire bus having a first wire and a second wire extending from the two feed-throughs of the implant controller to the two feed-throughs of each of the two or more electrode cells interconnecting the implant controller and the two or more electrode cells in parallel to carry on the first wire the first bus signal formed by the first time-varying power signal with the command signal modulated thereon, and to carry on the second wire the second bus signal formed by the second time-varying power signal and the command signal modulated therein.

2. The system according to claim 1, wherein, in operation, when recovered commands select an electrode of at least one of the electrode cells to deliver a stimulus, the control logic within the selected cell uses the commands to control the selected electrode to deliver extracted charge, in cooperation with at least one other electrode.

3. The system according to claim 2, a stimulus is delivered in the form of a biphasic pulse which have an anodic and a cathodic phase, with matched charge in each phase.

4. The system according to claim 3, wherein the control logic of each electrode cell is further operable to recover timing information from at least one of the first bus signal and the second bus signal to coordinate a selected electrode to step through anodic and cathodic phases of the biphasic pulse in cooperation with at least one other electrode.

5. The system according to claim 4, wherein the timing information is in the form of crossovers in at least one of the first bus signal and the second bus signal.

6. The system according to claim 4, wherein the timing information is in the form of crossovers with fixed frequency.

7. The system according to claim 3 wherein the commands define the amplitude of each phase the biphasic pulse and whether the biphasic pulse is cathodic or anodic in the first phase.

8. The system according to claim 1, wherein, in operation, recovered commands select plural electrodes to make telemetry measurements.

9. The system according to claim 8, wherein the selected electrodes make measurements in sequence and deliver telemetry measurements to the implant controller.

10. The system according to claim 1, wherein commands are modulated onto the power signal using phase modulated pulse pairs.

11. The system according to claim 1, wherein the implant controller and electrode cells each comprise a switch to selectively allow the flow of stimulus current from the implant controller to the electrode cell, and vice versa, and to control the direction of stimulus current.

12. The system according to claim 1, wherein the control logic in both the implant controller or electrode cells, or both, are provided by a processor or programmable logic array.

13. The system according to claim 1, wherein at least one of the electrode cells stores commands for more than one stimulation.

14. The system according to claim 1, wherein more than two electrode cells take part in generating a stimulus.

15. An implantable implant controller for delivering neuro-stimulation, including:
two feed-throughs to provide electrical pathways for a first bus signal and a second bus signal; and
control logic to transmit a first time-varying power signal and a second time-varying power signal, the first time-varying power signal and the second time-varying power signal varying between two levels, the first time-varying power signal varying in opposite phase to the second time-varying power signal, the first time-varying power signal forming the first bus signal, the second time-varying power signal forming the second bus signal, and to modulate a command signal onto the first power signal and the second power signal;
wherein, in operation, the implant controller is connectable to plural electrode cells by a two-wire bus having a first wire and a second wire, the first wire operable to carry the first bus signal formed by the first time-varying power signal with the command signal modulated thereon, the second wire operable to carry the second bus signal formed by the second time-varying power signal with the command signal modulated therein, each electrode cell having two feed-throughs to provide electrical pathways for the first bus signal and the second bus signal, each electrode cell having control logic to extract charge from at least one of the first bus signal and the second bus signal and recover commands from the first bus signal or the second bus signal, and the two-wire bus extends from the two feed-throughs of the implant controller to the two feed-throughs of each of the two or more electrode cells.

16. The controller according to claim 15, wherein, in operation, when recovered commands select an electrode of the electrode cell to deliver a stimulus, the control logic within the selected cell uses the commands to control the selected electrode to deliver extracted charge, in cooperation with at least one other electrode.

17. The controller according to claim 15, further comprising a reference electrode and a multi-pole switch to selectively connect the reference electrode to a voltage source, a current source or an open circuit to coordinate delivery of the stimulus.

18. The controller according to claim 15, further comprising control logic and an alternator to deliver the first time-varying power signal and the second time-varying power signal; and a clock and data transmitter to modulate at least one of the first time-varying power signal and the second time-varying power signal with clock and data signals.

19. An implantable electrode cell for delivering neuro-stimulation, including:
two feed-throughs to provide electrical pathways for a first bus signal formed by a first time-varying power signal and a second bus signal formed by a second time-varying power signal, the first time-varying power signal and the second time-varying power signal, varying between two levels, the first time-varying power signal being in opposite phase to the second time-varying power signal, and a command signal modulated onto the first time-varying power signal and the second time-varying power signal;
at least one electrode; and
control logic to extract charge from at least one of the first bus signal and the second bus signal to recover commands from the first bus signal or the second bus signal, and to deliver extracted charge to the electrode;
wherein the electrode cell is connectable to an implant controller and at least one other electrode cell by a two-wire bus having a first wire and a second wire, the implant controller having two feed-throughs to provide electrical pathways for the first bus signal and the second bus signal and control logic to form the first bus signal and the second bus signal, the two wire bus operable to carry on the first wire the first bus signal formed by the first time-varying power signal with the command signal modulated therein, to carry on the second wire the second bus signal formed by the second time-varying power signal with the command signal modulated thereon, and extend from the two feed-throughs of the implant controller to the two feed-throughs of the electrode cells.

20. The electrode cell according to claim 19, wherein, in operation, when recovered commands select an electrode of the electrode cell to deliver a stimulus, the control logic within the selected cell uses the commands to control the selected electrode to deliver extracted charge, in cooperation with at least one other electrode.

21. The electrode cell according to claim 20, wherein the stimulus is a biphasic pulse having anodic and cathodic phases.

22. The electrode cell according to claim 21, wherein the control logic is further operable to recover timing information from at least one of the bus signals to coordinate a selected electrode to step through anodic and cathodic phases of the biphasic pulse in cooperation with at least one other electrode.

23. The electrode cell according to claim 22, further comprising a multi-pole switch to selectively connect an electrode to a voltage source, a current source or an open circuit to coordinate delivery of a stimulus.

24. The electrode cell according to claim 23, wherein the control logic in the electrode cell is housed in a chip.

25. The electrode cell according to claim 24, wherein the chip provides a substrate for mounting the following components:
a rectifier and storage capacitor to extract charge from at least one of the first bus signal and the second bus signal;
a clock and data receiver to recover clock and data signals from the first bus signal; and
a current source to deliver extracted charge to an electrode.

26. A method of operating an implantable electrode cell for delivering neuro-stimulation, comprising the steps of:
- receiving a first bus signal formed by a first time-varying power signal, and a second bus signal formed by a second time-varying power signal, the first time-varying power signal and the second time-varying power signal varying between two levels, the first time-varying power signal being in opposite phase to the second time-varying power signal, and a command signal modulated onto the first time-varying power signal and the second time-varying power signal;
- determining whether the first bus signal is addressed to the electrode cell;
- if the electrode cell has more than one electrode, determining which electrode is selected;
- directing electrical charge from at least one of the first bus signal and the second bus signal to an on-board current source;
- recovering commands from the first bus signal or the second bus signal;
- setting the current of the current source to the value defined by the recovered commands,
- connecting the electrode to the on-board current source at a first time prescribed by the recovered commands; and
- disconnecting the electrode from the current source at a second time prescribed by the recovered commands.

27. A pair of signals for transmission between an implant controller and an electrode cell, comprising:
- a first time-varying power signal, a second time-varying power signal, the first time-varying power signal and the second time-varying power signal varying between two levels the first time-varying power signal being in opposite phase to the second time-varying power signal;
- wherein the first time-varying power signal and second time-varying power signal are modulated to represent a command, the command selecting an electrode of at least one of the electrode cells to deliver a stimulus, and
- control logic within the selected cell that uses the command modulated onto the first time-varying power signal or the second time-varying power signal to control the selected electrode to deliver charge extracted from at least one of the first time-varying power signal and second time-varying power signal, in cooperation with at least one other electrode.

28. The signals according to claim 26, wherein commands are modulated using differential pulse phase modulation.

* * * * *